United States Patent [19]

Mayer

[11] 4,081,451
[45] Mar. 28, 1978

[54] PROCESS FOR PREPARING 2-HALOGENO NICOTINIC ACIDS

[75] Inventor: Joseph Mayer, New York, N.Y.

[73] Assignee: Schering Corporation, Kenilworth, N.J.

[21] Appl. No.: 784,095

[22] Filed: Apr. 4, 1977

Related U.S. Application Data

[63] Continuation-in-part of Ser. No. 558,531, Mar. 20, 1975, abandoned, which is a continuation-in-part of Ser. No. 430,965, Jan. 4, 1974, abandoned, which is a continuation-in-part of Ser. No. 298,195, Oct. 17, 1972, abandoned, which is a continuation of Ser. No. 150,808, Jun. 7, 1971, abandoned, which is a continuation-in-part of Ser. No. 845,907, Jul. 29, 1969, abandoned.

[51] Int. Cl.$^2$ ............................................. C07D 213/55
[52] U.S. Cl. ........................... 260/295.5 R; 260/294.9
[58] Field of Search ................................. 260/295.5 R

[56] References Cited

PUBLICATIONS

Taylor et al., J. Am. Chem. Soc., vol. 77, pp. 5445–5446 (1955).

*Primary Examiner*—Alan L. Rotman
*Attorney, Agent, or Firm*—Carver Joyner; Stephen B. Coan; Raymond McDonald

[57] ABSTRACT

This invention relates to a novel process for preparing 2-halogeno-nicotinic acids. The compounds, especially 2-chloro-nicotinic acid, are intermediates in the preparation of anilino nicotinic acid derivatives. The latter compounds are useful as analgesic anti-diarrheal and anti-inflammatory agents.

18 Claims, No Drawings

PROCESS FOR PREPARING 2-HALOGENO NICOTINIC ACIDS

This application is a continuation-in-part of copending application Ser. No. 558,531, filed Mar. 20, 1975, now abandoned which in turn is a continuation-in-part of (now abandoned) Application Ser. No. 430,965, filed Jan., 1974, which in turn is a continuation-in-part of Application Ser. No. 298,195, filed Oct. 17, 1972 (now abandoned), which in turn is a continuation of Application Ser. No. 150,808, filed June 7, 1971 (now abandoned) which application is in turn a continuation-in-part of Application Ser. No. 845,907, filed July 29, 1969, (now abandoned).

This invention relates to a method for preparing 2-halogeno-nicotinic acids. More particularly, it relates to preparing 2-halogeno-nicotinic acids having substituents selected from the group consisting of bromine, alkyl, phenyl or benzyl at positions 5.

In one method commonly used to prepare 2-halogeno-nicotinic acids, a 2-amino-3-methyl pyridine (2-amino-$\beta$-picoline) is utilized as the starting material. The compound is subjected to a diazotization followed by a Sandmeyer replacement of the diazonium salt with a halogen. The thus formed 2-halogeno-3-methyl-pyridine is then subjected to an oxidation reaction to yield the desired 2-halogeno-nicotinic acid. As a laboratory process, where yields and consequently costs are of a secondary importance, the foregoing process has utility. Even on a laboratory scale, however, the diazotization step is difficult to control; and in those instances wherein the reaction becomes too vigorous, a concomitant loss in yield often results. It thus becomes obvious to one skilled in the art that the above-described process is not suitable for large scale manufacturing and will give erratic results with wide variations in product quality from batch-to-batch. This procedure necessitates the oxidation of a 2-halogeno-3-methyl-pyridine to the corresponding 2-halogeno-nicotinic acid; therefore, it is normally not applicable to compounds having an alkyl or a benzyl substituent in either of positions 5.

According to the instant invention, it now has been found that 2-halogeno-nicotinic acids including those having the above-named substituents may be prepared in yields that are reproducible and substantially higher than prior art methods. Further, the instant process gives a product that is essentially uniform and in a state of high purity. Moreover, the reactants needed to effect the instant process are commercially available or may be synthesized from readily available low-cost intermediates.

The invention sought to be patented may be described as residing in the concept of converting a 3-cyano-2-pyridone (or a 5-substituted analog thereof) to a 2-hydroxy nicotinic acid (or a 5-substituted analog thereof) and transforming the thus formed 2-hydroxy-nicotinic acid (or analog thereof) into the appropriately substituted 2-halogeno-nicotinic acid.

The 2-halogeno-nicotinic acids, especially 2-chloronicotinic acid are valuable intermediates in the preparation of anilino nicotinic acid derivatives, the latter compounds being useful as analgesic agents such as, for example, 2-(2-methyl-3-nitro-anilino)-nicotinic acid. The anilino nicotinic acid derivatives are also useful as anti-inflammatory agents, one such compound being 2-(2-methyl-3-chloroanilino)-nicotinic acid, which is disclosed in U.S. Pat. No. 3,689,653, issued Sept. 5, 1972. Particularly useful R-substituted anilino nicotinic acid compounds are those derived from 2-halogeno-nicotinic acids having at positions 5 such substituents as bromine, methyl, ethyl, propyl, benzyl and phenyl. Anilino nicotinic acids having a bromo substituent at positions 5 of the nicotinic acid moiety also exhibit anti-diarrheal activity. In view of their end use, it is of substantial importance that the process by which the 2-halogeno-nicotinic acids are produced afford an excellent yield. It is also essential that the products obtained be of a high degree of purity to obviate the need for further purification thereby avoiding the added cost incident to further processing. The instant process provides the above-stated advantages and is uniquely suited for the preparation of such valuable intermediates.

The instant invention may be described as a process comprising the following steps:

(a) hydrolyzing an R-substituted-3-cyano-2-pyridone to an R-substituted-2-hydroxy-nicotinic acid, (b) reacting the R-substituted-2-hydroxy-nicotinic acid with a phosphorous oxyhalide alone or in admixture with a phosphorous pentahalide, to form an R-substituted-2-halogeno-nicotinoyl halide and, (c) hydrolyzing the R-substituted-2-halogeno-nicotinoyl halide to an R-substituted-2-halogeno-nicotinic acid.

The above-described process may be depicted by the following reaction sequences.

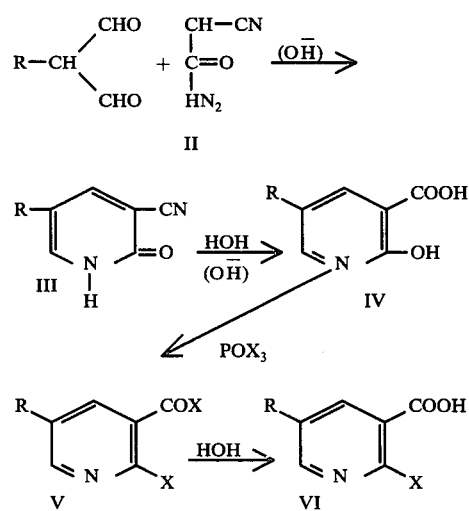

As indicated above, the starting material generally employed in the process is R-substituted-3-cyano-2-pyridone (I) for which there is known in the art several methods of preparation. One very facile method is the base catalyzed condensation of cyanoacetamide and an R-substituted malondialdehyde. The condensation is generally effected by reacting the cyanoacetamide and the malondialdehyde in the presence of a suitable base at a temperature in the range of from about 5° C to about 95° C. The bases used to effect the condensation may be organic or inorganic. The organic bases may be completely or only slightly miscible with water. Exemplary of the foregoing are such bases as sodium hydroxide, ammonium hydroxide, potassium hydroxide, disodium phosphate, trimethylamine, pyridine, triethylamine, tri-n-propylamine (two phase system), piperidine and the like. The progress of the condensation may be conveniently followed by ultraviolet spectroscopy, 3-cyano-2-pyridone, having a characteristic peak in an aqueous solution at about 325 mμ (ε = 8100).

In those instances wherein the 3-cyano-2-pyridone bears a 5-R-substituent other than hydrogen (i.e. a bromo, lower alkyl, phenyl or benzyl substituent), it may be prepared by substantially the same procedure (i.e. condensing cyanoacetamide with the appropriately substituted 1,3-dicarbonyl reactant).

Hydrolysis of the 3-cyano-2-pyridone to 2-hydroxy-nicotinic acid (IV) is effected by heating the pyridone at from about 60° C to about 180° C in water or a suitable organic solvent with the simultaneous addition of concentrated aqueous base and vigorous stirring. The bases generally employed to effect the instant hydrolysis are the alkali metal and alkaline earth metal hydroxides with sodium and potassium hydroxide being preferred. The hydrolysis is usually effected at a pH range of from about 10 to about 14 with the higher pH being preferred. It is, of course, to be noted that under such basic conditions both the acid and the phenolic hydroxyl form salts with the alkali or alkaline earth metal hydroxide. The base is usually employed in the range of about 2 to 20 moles per mole of pyridone with about 3 to about 6 moles per mole of 3-cyano-2-pyridone being preferred. As the basic solution begins to reflux, the evolution of ammonia gas commences. The refluxing is continued for from about 1 to about 4 hours, preferably for about 2 hours. Alternatively, the reaction is continued for about one hour after the evolution of ammonia ceases. The reaction mixture is cooled, the solution acidified and the product removed by filtration. The reaction can be effected in a wide range of solvents with which the concentrated aqueous base is miscible. Exemplary of such solvents are the lower alcohols (e.g. methanol, ethanol, propanol and butanol), glycols, such as ethylene glycol and propylene glycol, and cyclic ethers such as tetrahydrofuran, dioxane and the like. In those instances wherein the reaction is conducted exclusively in aqueous base, acidification of the solution induces the precipitation of the 2-hydroxy-nicotinic acid. When an organic solvent is used, isolation of the 2-hydroxy-nicotinic acid is usually preceded by the partial or complete removal of the organic solvent.

Hydrolysis of the 3-cyano-2-pyridone to 2-hydroxy-nicotinic acid is also effected by heating the pyridone in an aqueous medium containing a molar excess of a strong acid. In general, strong acids are the mineral and sulfonic acids such as hydrochloric acid, sulfuric acid, phosphoric acid, perchloric acid, methanesulfonic acid, benzenesulfonic acid, p-toluenesulfonic acid and the like. For example, when the pyridone is heated at reflux in a medium comprising from about 2 to about 10 volumes of concentrated hydrochloric acid, conversion to 2-hydroxy-nicotinic acid is substantially complete in about 3 to 6 hours. The 2-hydroxy-nicotinic acid may be isolated directly from the reaction medium by cooling.

Transformation of the 2-hydroxy-nicotinic acid to the 2-halogeno-nicotinic acid (VI), is effected by treating the acid with a phosphorous oxyhalide alone or in admixture with a phosphorous pentahalide for from about 2 to about 10 hours, preferably about 4–6 hours. The phosphorous oxyhalide may be utilized as the solvent in addition to its role as a reactant. Consequently, it may be employed at almost any quantity above two moles per mole, when the transformation is carried out using both phosphorous oxyhalide and phosphorous pentahalide, the pentahalide is employed at about 1 more per mole of 2-hydroxy-nicotinic acid. Alternatively, the transformation may be carried out in other solvents such as benzene, toluene, xylene, chloroform, ethylene dichloride, propyl ether, isopropyl ether, butylether, and other nonreactive organic solvents. In general, the reaction is effected at a temperature range of from about 60° C to about 110° C, preferably, at the boiling temperature of the reaction mixture. The reaction mixture is worked-up by quenching the reaction with ice and water with vigorous stirring. The primary reaction product is the 2-halogeno-nicotinoyl halide which precipitates during the quenching operation but is readily hydrolyzed to the free carboxylic acid by warming the resulting aqueous suspension at a temperature range of from about 5° C to about 100° C preferably 35° C to 45° C for from about 10 to about 120 minutes until the hydrolysis is substantially complete. The pH of the suspension is adjusted to about 1 to 5, preferably about 1 to 3, by the addition or aqueous base and the product isolated.

The 2-halogeno acid halide (e.g. 2-chloro-nicotinoyl chloride) may be isolated, if in the foregoing procedure, the temperature is kept at about 5° C during the quenching step and the precipitate is filtered quickly and dried in vacuo at about 25° C. The product decomposes upon prolonged exposure to moisture and for this reason, should preferably be converted in situ to the carboxylic acid which is considerably more stable.

When a non-reactive organic solvent is employed in the formation of 2-halogeno-nicotinic acid (VI) the product may be isolated by the procedure described above or, alternatively, the organic solvent may be removed by steam distillation and the product subsequently isolated.

The best mode contemplated by applicant for carrying out the process of this invention is illustrated in the following examples.

EXAMPLE 1

2-Chloro-Nicotinic Acid

A. 2-Hydroxy-Nicotinic Acid

Heat a mixture containing 60 g of 3-cyano-2-pyridone, 25 ml. of water and 62 g of 45% of aqueous potassium hydroxide solution to reflux and, over a 20 minute period, add dropwise an additional 125 g of 45% aqueous potassium hydroxide solution. During this operation the evolution of ammonia gas commences. Continue refluxing the mixture for about 1 hour after the evolution of ammonia gas ceases. Cool the reaction mixture to room temperature then pour it into an ice cold solution containing about 5–10% excess hydrochloric acid. The resulting mixture should be acid to congo red, if not, add additional hydrochloric acid. Stir the resulting mixture for several hours at about 5° C and filter. Wash the precipitate with cold water and dry at about 65° C obtaining thereby 2-hydroxy-nicotinic acid, m.p. 257°–260° C.

B. 2-Chloro-Nicotinic Acid

Heat a mixture consisting of 70 g of 2-hydroxy-nicotinic acid and 160 ml. of phosphorous oxychloride to reflux and hold for 3 hours. Concentrate the solution in vacuo to a residue and add 100 ml. of warm toluene with vigorous stirring. With external cooling, add slowly 700 ml. of ice and water while maintaining the internal temperature below 80° C. Cool the reaction mixture to 5°–15° C, adjust the pH to about 2.0 by the addition of aqueous sodium hydroxide and collect the precipitate by filtration obtaining thereby 2-chloro-nicotinic acid, m.p. 180°–181° C.

EXAMPLE 2

2-Chloro-Nicotinic Acid

A. 2-Hydroxy-Nicotinic Acid

Prepare a solution containing 6 g of 3-cyano-2-pyridone, 7.5 g of potassium hydroxide pellets (85%), 8 ml. of ethylene glycol and 1.5 ml. of water. Heat the solution to 150°–160° C for 15 minutes and pour the reaction mixture into ice water. Acidify the aqueous solution to a pH of about 3. The 2-hydroxy-nicotinic acid precipitates, is collected by filtration and dried yielding the product of this step, m.p. 258°–260° C.

B. 2-Chloro-Nicotinoyl Chloride

Heat a mixture of 3.5 g of 2-hydroxy-nicotinic acid and 4.2 ml. of phosphorous oxychloride on a steam bath for 7 hours and cautiously pour the reaction mixture on ice and water keeping the temperature at about 5° C. Filter the suspension and wash the precipitate thoroughly with ice water. Dry the product at room temperature in vacuo and obtain thereby 2-chloro-nicotinoyl chloride, m.p. 38°–40° C.

C. 2-Chloro-Nicotinic Acid

Suspend the 2-chloro-nicotinoyl chloride in water and warm to about 35°–45° C whereupon 2-chloro-nicotinic acid is formed in partically quantitative yield.

EXAMPLE 3

2-Chloro-Nicotinic Acid

A. 2-Hydroxy-Nicotinic Acid

Reflux a mixture consisting of 48 g of 3-cyano-2-pyridone and 200 ml. of 10N hydrochloric acid for about 5 hours. Cool the reaction mixture to about 10°–15° C and hold for several hours. Filter the acidic suspension, wash the precipitate with ice water and dry to obtain 2-hydroxy-nicotinic acid, m.p. 259°–260° C.

B. 2-Chloro-Nicotinic Acid

Heat a mixture consisting of 24.4 g of 2-hydroxy nicotinic acid and 42 ml. of phosphorous oxychloride to 100°–108° C and hold for 1 hour. Add 36.4 g of phosphorous pentachloride and heat the resulting mixture at reflux for another hour. Remove the excess phosphorous oxychloride in vacuo and pour the viscous residue on ice with stirring. Age the resulting slurry at room temperature for about 12 hours. The slurry is filtered, washed and dried to yield 2-chloro-nicotinic acid, m.p. 190° C.

In a similar manner, by substituting an equivalent quantity of 5-E-3-cyano-2-pyridone (prepared from R-substituted malonic dialdehyde) in the process of Example 3, step A and by following the procedure of steps A and B, the corresponding 5-R-substituted-2-chloro-nicotinic acids may be prepared. Exemplary of such substituents are bromo, methyl, ethyl, propyl, isopropyl, phenyl and benzyl.

I claim:

1. A process for the preparation of a 5-R-2-halogeno nicotinic acid having the formula:

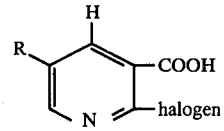

wherein R is a member of the group consisting of hydrogen, bromo, alkyl, phenyl and benzyl which comprises the following steps:
   (a) hydrolyzing an R-substituted-3-cyano-2-pyridone to obtain an R-substituted-2-hydroxy-nicotinic acid,
   (b) reacting said R-substituted-2-hydroxy-nicotinic acid with a phosphorous oxyhalide and,
   (c) hydrolyzing the so-produced R-substituted-2-halogeno-nicotinoyl halide to the corresponding R-substituted-2-halogeno-nicotinic acid.

2. A process for preparing an R-substituted-2-halogeno-nicotinic acid wherein R is a member of the group consisting of hydrogen, bromine, alkyl, phenyl and benzyl and wherein R is a substituent at one of position 5, which comprises hydrolyzing a 5-R-2-halogeno-nicotinoyl halide in an aqueous medium having a temperature in the range of from about 5° C to about 100° C.

3. A process for preparing an R-substituted-2-halogeno nicotinoyl halide wherein R is a member selected from the group consisting of hydrogen, bromine, alkyl, phenyl and benzyl and wherein R is a substituent at one of positions 5 which comprises reacting a 5-R-2-hydroxy-nicotinic acid with a phosphorous oxyhalide at a temperature of from about 60° C to about 110° C.

4. The process of claim 1 wherein the hydrolysis of the R-substituted-3-cyano-2-pyridone is effected in an alkaline medium in at a temperature range of from about 60° C to about 180° C.

5. The process of claim 4 wherein the hydrolysis is effected in the presence of an alkali metal hydroxide.

6. The process of claim 1 wherein the hydrolysis of the R-substituted-3-cyano-2-pyridone is effected in a strongly acid medium.

7. The process of claim 6 wherein the hydrolysis is effected in the presence of a mineral acid.

8. The process of claim 3 wherein the R-substituted-2-hydroxy-nicotinic acid is reacted with a phosphorous oxyhalide in admixture with a phosphorous pentahalide.

9. The process of claim 8 wherein the phosphorous oxyhalide is phosphorous oxychloride.

10. The process of claim 8 wherein the phosphorous pentahalide is phosphorous pentachloride.

11. The process of claim 1 wherein the R-substituted-2-halogeno-nicotinoyl halide is hydrolyzed in an aqueous medium having a temperature in the range of about 5° C to about 100° C.

12. The process of claim 1 for producing an R-substituted-2-chloro-nicotinic acid which comprises the following steps:
   (a) hydrolyzing an R-substituted-3-cyano-2-pyridone in a strongly acid aqueous medium to produce an R-substituted-2-hydroxy-nicotinic acid,
   (b) reacting the R-substituted-2-hydroxy-nicotinic acid with phosphorous oxychloride to produce an R-substituted-2-chloro-nicotinoyl chloride, and,
   (c) hydrolyzing the so-produced R-substituted-2-chloro-nicotinoyl chloride in an aqueous medium at a temperature in the range of about 5° C to about 100° C.

13. The process of claim 12 wherein step *b* is effected in the presence of phosphorous pentachloride.

14. The process of claim 12 wherein step *a* is effected in the temperature range of about 60° C to 100° C, step *b* is effected in the temperature range of 60° C to 110° C, and step *c* is effected in the temperature range of about 5° C to 100° C.

15. The process of claim 1 for preparing an R-substituted-2-chloro-nicotinic acid which comprises the following steps:
 (a) hydrolyzing an R-substituted-3-cyano-2-pyridone in a medium having a pH in the range of from about 10 to about 14 wherein said medium contains a member selected from the group consisting of alkali metal and alkaline earth metal hydroxides to form an alkali metal or alkaline earth metal salt of an R-substituted-2-hydroxy-nicotinic acid,
 (a') Converting said salt to an R-substituted-2-hydroxy-nicotinic acid,
 (b) reacting the R-substituted-2-hydroxy-nicotinic acid with phosphorous oxychloride to produce an R-substituted 2-chloro-nicotinoyl chloride, and
 (c) hydrolyzing the so-produced R-substituted-2-chloro-nicotinoyl chloride in an aqueous medium at a temperature in the range of about 5° C to about 100° C.

16. The process of claim 15 wherein step *b* is effected in the presence of phosphorous pentachloride.

17. The process of claim 2 wherein the hydrolysis is effected at a temperature of from about 35° C to about 45° C.

18. The process of claim 5 wherein the hydrolysis is effected at a temperature of from about 150° C to about 160° C.

* * * * *